US006923755B2

(12) United States Patent
Norma

(10) Patent No.: US 6,923,755 B2
(45) Date of Patent: Aug. 2, 2005

(54) STIMULATOR

(76) Inventor: Marco Norma, 4835 Lakeview Dr., Miami Beach, FL (US) 33140

(*) Notice: Subject to any disclaimer, the term of this patent is extended or adjusted under 35 U.S.C. 154(b) by 11 days.

(21) Appl. No.: 10/728,966

(22) Filed: Dec. 8, 2003

(65) Prior Publication Data

US 2005/0124853 A1 Jun. 9, 2005

(51) Int. Cl.$^{7}$ .............................. A61F 5/00; A61F 1/00
(52) U.S. Cl. .......................................... 600/38; 601/70
(58) Field of Search ...................... 600/38–41; 601/46, 601/79, 80, 67, 78; 433/159, 160, 4; 140/106, 140/121; 606/205–211, 133; 81/416, 319, 81/321–324, 328; 428/49

(56) References Cited

U.S. PATENT DOCUMENTS 6,053,881 A * 4/2000 Boodramsingh et al. ...... 601/70
6,056,705 A * 5/2000 Stigar-Brown ............... 601/84
6,685,660 B1 * 2/2004 Taverna et al. ............... 601/81
2003/0181784 A1 * 9/2003 Klein ......................... 600/38

OTHER PUBLICATIONS

Adam & Eve Catalog from Nov. 29, 2001, cover and p. 11.*

* cited by examiner

*Primary Examiner*—Samuel G. Gilbert
(74) *Attorney, Agent, or Firm*—J. Sanchelima; A. Bordas

(57) ABSTRACT

A clitoris stimulator having a vibrating device with a clip assembly adapted to be removably attached to the vaginal labia of a user. The clip assembly removably attaches to the vaginal labia to cooperatively bring in contact the vibrating device to the clitoris area. In an alternate embodiment, the clip assembly is mounted to a holder, instead of the vibrating member, and the holder cooperates to receive the vibrating member. The holder comes in contact with the clitoris area. In still another embodiment the clip assembly is mounted to the vibrating device directly. In all embodiments a sufficient and comfortable gripping action is exerted on the labia to keep the stimulator in place.

4 Claims, 3 Drawing Sheets

STIMULATOR

BACKGROUND OF THE INVENTION

1. Field of the Invention

The present invention relates to a clitoris stimulator, and more particularly, to such a device that can be used without requiring further manipulation by a user.

2. Description of the Related Art

Several designs for clitoris stimulator have been designed in the past. None of them, however, includes means for removably attaching it to the vaginal labia to cooperatively bring a vibrating element in abutting relationship with the clitoral area.

SUMMARY OF THE INVENTION

It is one of the main objects of the present invention to provide a stimulator for the clitoral area that can be utilized without requiring the user to hold it in place.

It is another object of this invention to provide a device that permits a user to engage in sexual intercourse while operating the stimulator.

It is still another object of the present invention to provide a simple non-invasive device that can effectively stimulate the clitoris.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
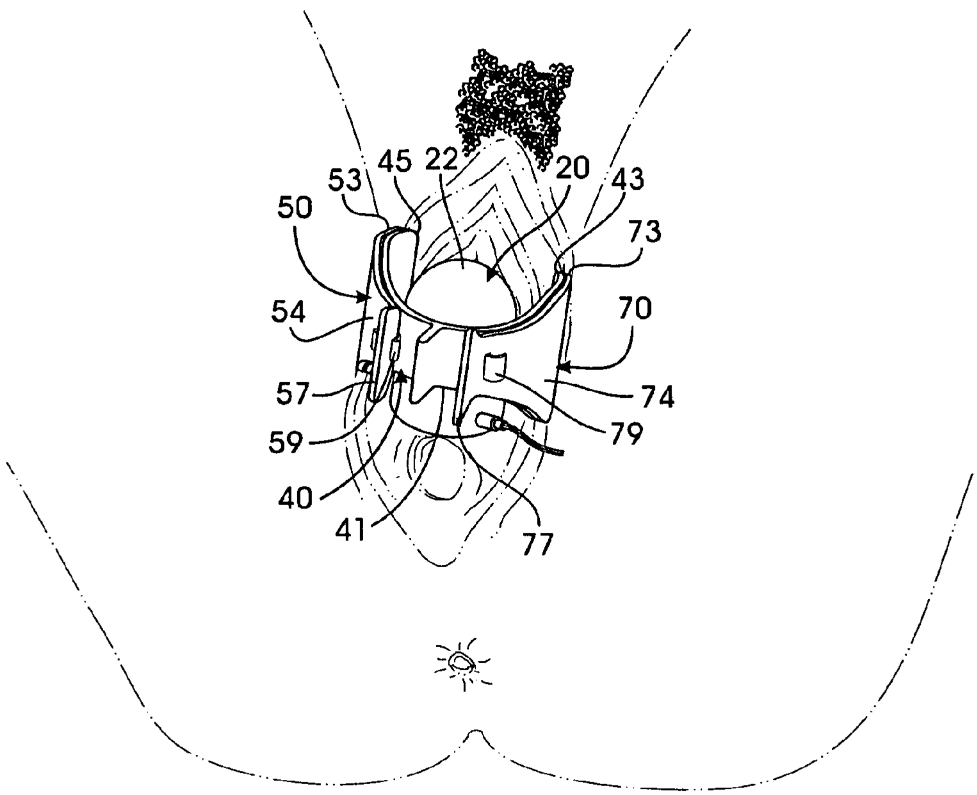
FIG. 1 represents an isometric view of the preferred embodiment for the clitoris stimulator, object of the present application, mounted to a female labia (shown in phantom).
Figure 2:
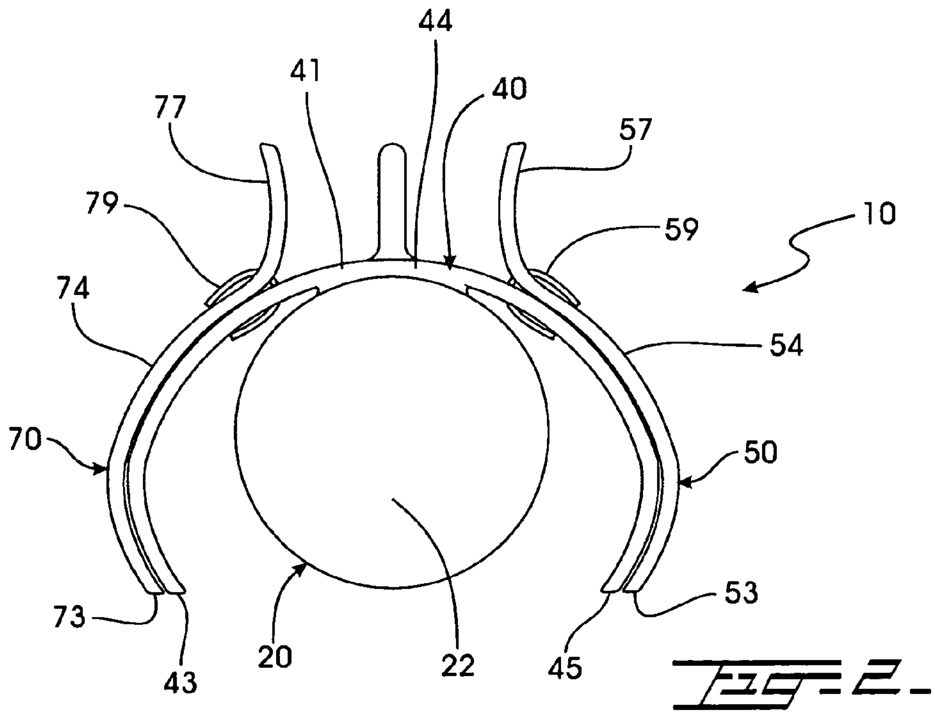
FIG. 2 shows a top view of the embodiment represented in figure one.

Referring now to the drawings, where the present invention is generally referred to with numeral 10, it can be observed that it basically includes vibrating device 20 and clip assembly 40, as seen in FIG. 1.

Vibrating device 20 may be operated with batteries or AC voltage. In the preferred embodiment, a washable material is used with a rounded end 22 that comes in contact with the clitoris.

Figure 3:
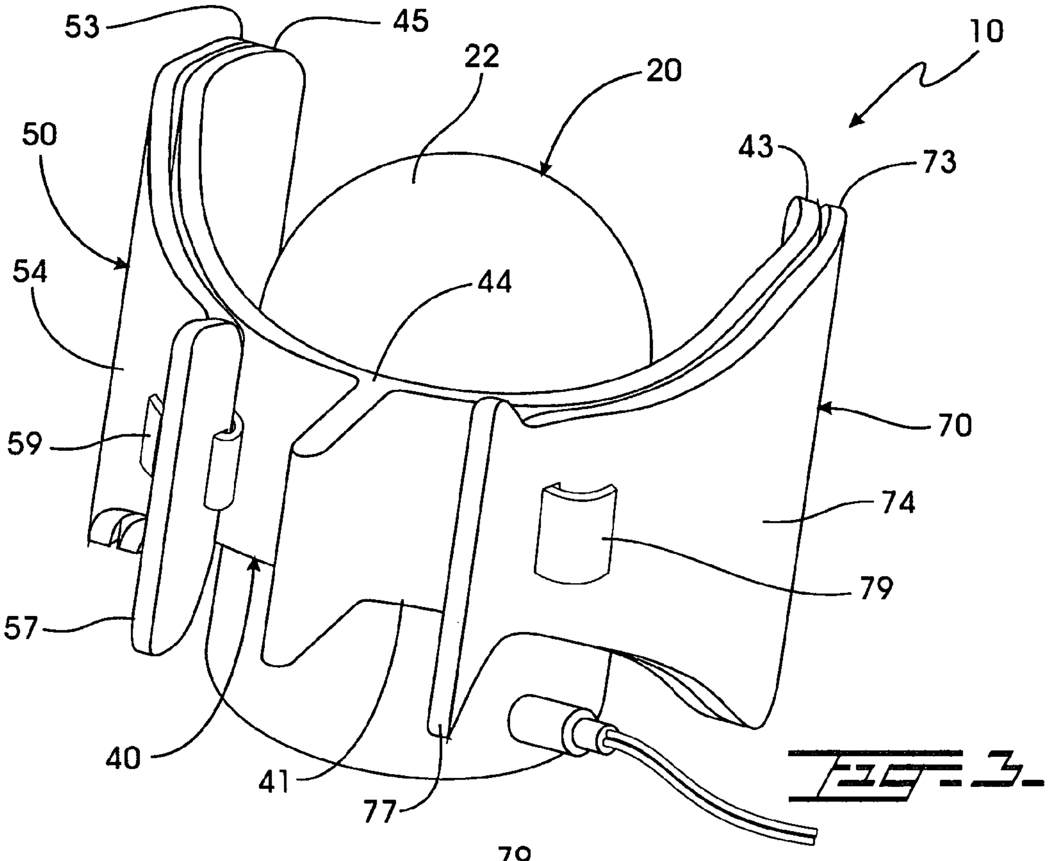
FIG. 3 illustrates an isometric view of the embodiment represented in figure one.
Figure 4:
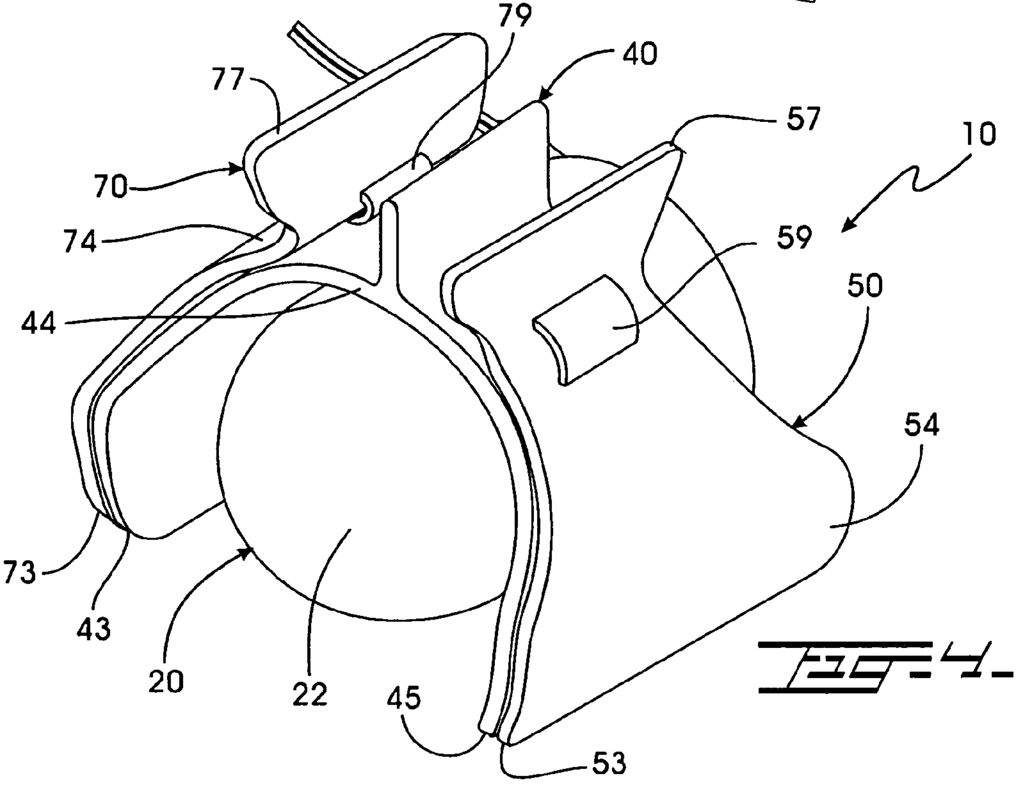
FIG. 4 is an isometric view of the embodiment represented in figure one, seen from another angle.

Clip assembly 40, as seen in FIGS. 1 and 3, includes a rigid curved plate 41 with ends 43 and 45. Central portion 44 of plate 41 is rigidly mounted to device 20 so that plate 41 partially surrounds it. Ends 43 and 45 extend and are positioned at a predetermined cooperative spaced apart relationship with respect to vibrating device 20. Movable arms 50 and 70 are hingedly mounted to plate 41 at their respective central portions 54 and 74. Arms 50 and 70 are actuated by pressing on end surfaces 57 and 77, respectively, causing ends 53 and 73 to separate by overcoming the bias of spring members 59 and 79, respectively. The separation is sufficient to permit the insertion of the edge of the vaginal labia (majora) and when released, the entire device is kept in place, preferably, with rounded end 22 in contact with the user's clitoris. The pressure exerted by spring members 59 and 79 is selected to avoid an uncomfortable grip.

Figure 5:
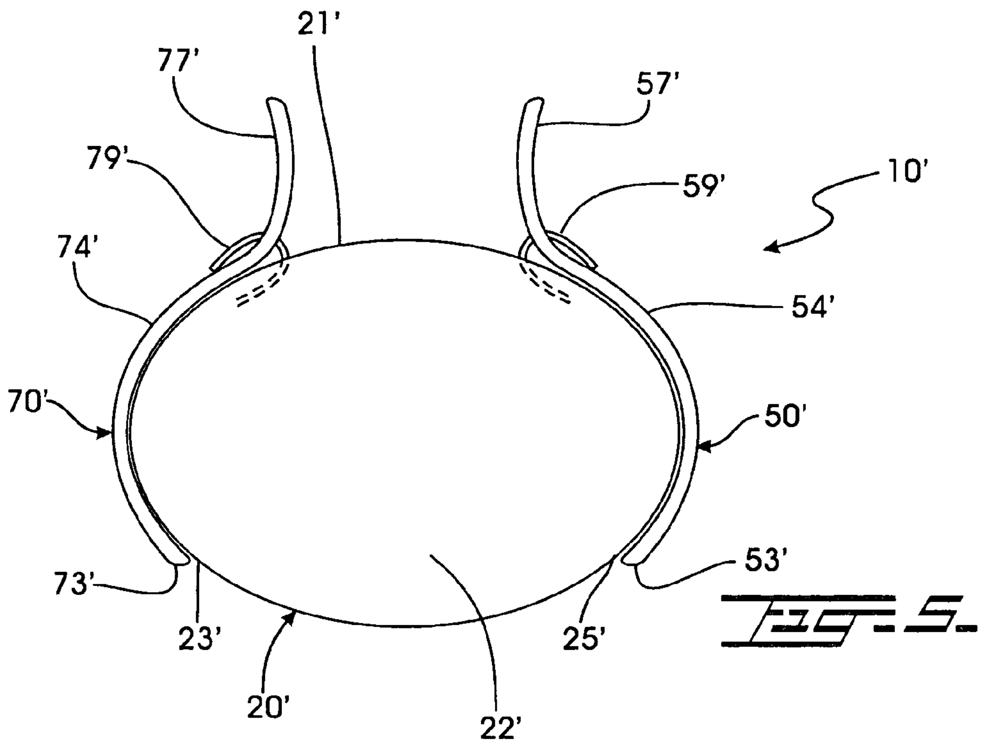
FIG. 5 shows a top view for an alternate embodiment for the present invention, where the clip assembly is mounted to the vibrating device directly.

An alternate embodiment of the present invention is shown in FIG. 5 and generally referred to with numeral 10'. Arms 50' and 70' are hingedly or pivotally mounted to predetermined positions on vibrating device 20' directly through spring members 59' and 79' at central positions 54' and 74'. Distal ends 53' and 73' are urged against areas 23' and 25' and in between a user's labia is inserted.

Figure 6:
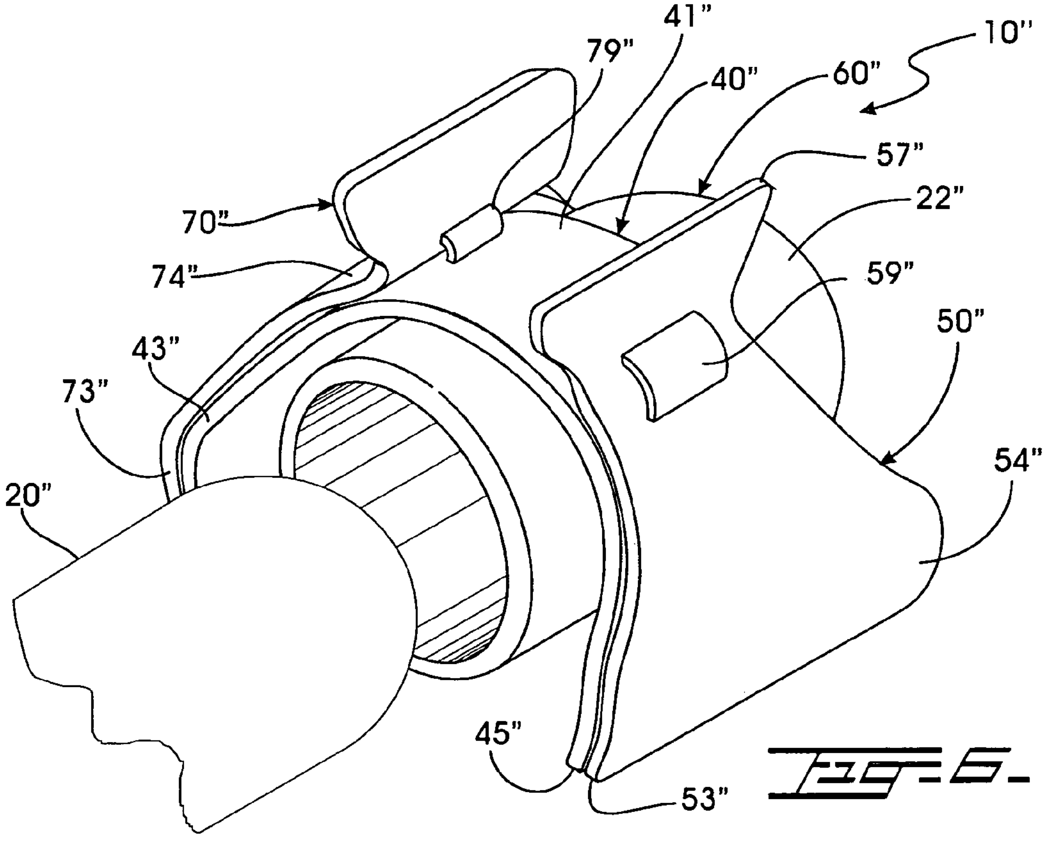
FIG. 6 illustrates an isometric view for another alternate for the present invention, where the vibrating device is removable received by a holder member.

Still another embodiment is shown in FIG. 6. A vibrating device 20" is used with cooperative dimensions to be received within holder 60". Clip assembly 40" is rigidly mounted to holder 60", and it functions like in the main embodiment as described above.

Curved plate 41" is rigidly mounted to holder 60" at its central portion thereby surrounding it. With this embodiment, a user can utilize a common vibrating device 20".

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A clitoris stimulator, comprising:

A) electrically driven vibrating means; and

B) clip means for removable attachment to the vaginal labia of a user, said clip means being mounted to said vibrating means so that said vibrating means is adapted to be kept in contact with the user's clitoris, said clip means includes first and second spring biased arm members cooperatively mounted to said vibrating means to provide sufficient gripping action against predetermined areas of said vibrating means so that a first portion of a user's labia on one side is adapted to be releasably held between said first arm and said vibrating means and a second portion of the labia on the opposite side is adapted to be releasably held between said second arm and said vibrating means.

2. The stimulator set forth in claim 1 wherein said clip means includes a rigid curved plate with a central portion, first and second ends, said central portion being rigidly mounted to said vibrating means and said first and second ends being kept at a spaced apart relationship with respect to said vibrating means so that said first and second arm members cooperate with said first and second ends adapted to provide sufficient grip action to a user's vaginal labia to keep said stimulator in place.

3. A clitoris stimulator, comprising:

A) electrically, driven vibrating means;

B) tubular holder means for removably receiving said vibrator means; and

C) clip means for removable attachment to the vaginal labia of a user, said clip means being mounted to said holder means, said clip means includes first and second spring biased arm members cooperatively mounted to said vibrating means to provide sufficient gripping action against predetermined areas of said vibrating means so that a first portion of a user's labia on one side is adapted to be releasably held between said first arm and said vibrating means and a second portion of the labia on the opposite side is adapted to be releasably held between said second arm and said vibrating means.

4. The stimulator set forth in claim 3 wherein said clip means includes a rigid curved plate with a central portion, first and second ends, said central portion being rigidly mounted to said vibrating means and said first and second ends being kept at a spaced apart relationship with respect to said holder means so that said first and second arm members cooperate with said first and second ends adapted to provide sufficient grip action on a user's vaginal labia to keep said stimulator in place.

* * * * *